US008897851B2

(12) United States Patent  
Caprio et al.

(10) Patent No.: US 8,897,851 B2
(45) Date of Patent: Nov. 25, 2014

(54) RELEASABLE LINER FOR SENSOR DEVICE

(75) Inventors: Matthew Caprio, Seattle, WA (US);
Andrew Clay, Everett, WA (US);
Jeffrey William Ladwig, Seattle, WA (US)

(73) Assignee: Verathon Inc., Bothell, WA (US)

( * ) Notice: Subject to any disclaimer, the term of this patent is extended or adjusted under 35 U.S.C. 154(b) by 0 days.

(21) Appl. No.: 13/183,310

(22) Filed: Jul. 14, 2011

(65) Prior Publication Data
US 2013/0018250 A1    Jan. 17, 2013

(51) Int. Cl.
*A61B 5/0408* (2006.01)
*A61B 5/00* (2006.01)

(52) U.S. Cl.
CPC ........... *A61B 5/04085* (2013.01); *A61B 5/6823* (2013.01); *A61B 5/6832* (2013.01)
USPC ............................ 600/389; 600/392; 600/393

(58) Field of Classification Search
CPC ........... A61B 5/04085; A61B 5/04087; A61B 5/6805; A61B 5/6823; A61B 5/6832
USPC ......................................... 600/392, 393, 389
See application file for complete search history.

(56) References Cited

U.S. PATENT DOCUMENTS

| | | | |
|---|---|---|---|
| 4,763,660 A * | 8/1988 | Kroll et al. | 600/391 |
| 5,184,620 A | 2/1993 | Cudahy et al. | |
| 5,191,887 A * | 3/1993 | Cartmell | 600/392 |
| 5,341,806 A | 8/1994 | Gadsby et al. | |
| 5,713,842 A * | 2/1998 | Kay | 602/57 |
| 5,868,671 A * | 2/1999 | Mahoney | 600/382 |
| 6,055,448 A * | 4/2000 | Anderson et al. | 600/372 |
| 6,115,638 A | 9/2000 | Groenke | |
| 6,141,575 A * | 10/2000 | Price | 600/393 |
| 6,301,493 B1 * | 10/2001 | Marro et al. | 600/383 |
| 6,415,169 B1 | 7/2002 | Kornrumpf et al. | |
| 6,553,247 B1 | 4/2003 | Rytky | |
| 6,711,427 B1 * | 3/2004 | Ketelhohn | 600/372 |
| 6,745,062 B1 * | 6/2004 | Finneran et al. | 600/393 |
| 7,027,877 B2 * | 4/2006 | Dupelle et al. | 607/142 |
| 7,173,437 B2 | 2/2007 | Hervieux et al. | |
| 7,206,630 B1 | 4/2007 | Tarler | |
| 7,211,053 B2 | 5/2007 | Marmaropoulos et al. | |
| 8,019,402 B1 | 9/2011 | Kryzpow et al. | |
| 2002/0072682 A1 | 6/2002 | Hopman et al. | |
| 2005/0251003 A1 | 11/2005 | Istvan et al. | |
| 2007/0155119 A1 | 7/2007 | Muemmler et al. | |
| 2008/0154110 A1 | 6/2008 | Burnes et al. | |
| 2008/0177168 A1 | 7/2008 | Callahan et al. | |
| 2010/0101733 A1 | 4/2010 | Yu Chen et al. | |
| 2011/0015498 A1 | 1/2011 | Mestrovic et al. | |

FOREIGN PATENT DOCUMENTS

JP     2009-72242      *  4/2009
WO     2009139911 A2     11/2009

* cited by examiner

*Primary Examiner* — Lee S Cohen
(74) *Attorney, Agent, or Firm* — Foster Pepper PLLC; Richard A. Koske; Richard C. Vershave

(57) ABSTRACT

A releasable liner for a sensor device having adhesive and conductive gel portions includes a flexible sheet having a free end and a fixed end, and a portion of the flexible sheet that is releasably attached to the sensor device, wherein the flexible sheet is folded upon itself so that the fixed end is generally adjacent the free end. Exerting a pulling force on the free end releases the liner in a controlled manner to uncover the adhesive and conductive gel portions of the sensor device.

5 Claims, 7 Drawing Sheets

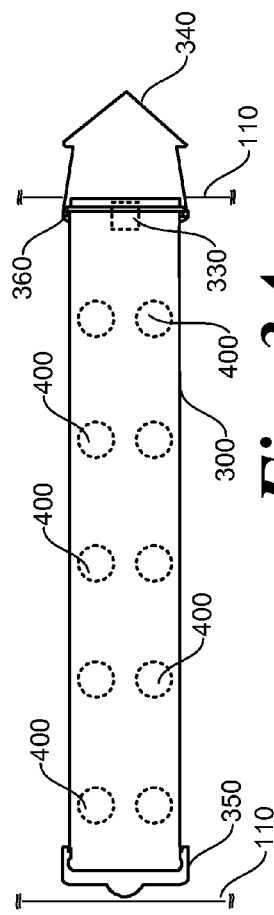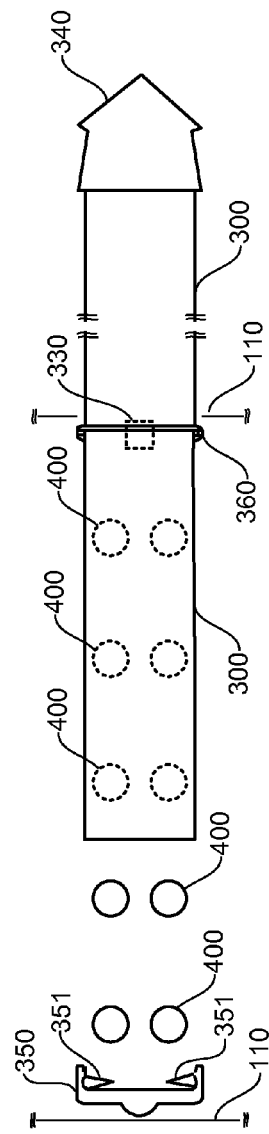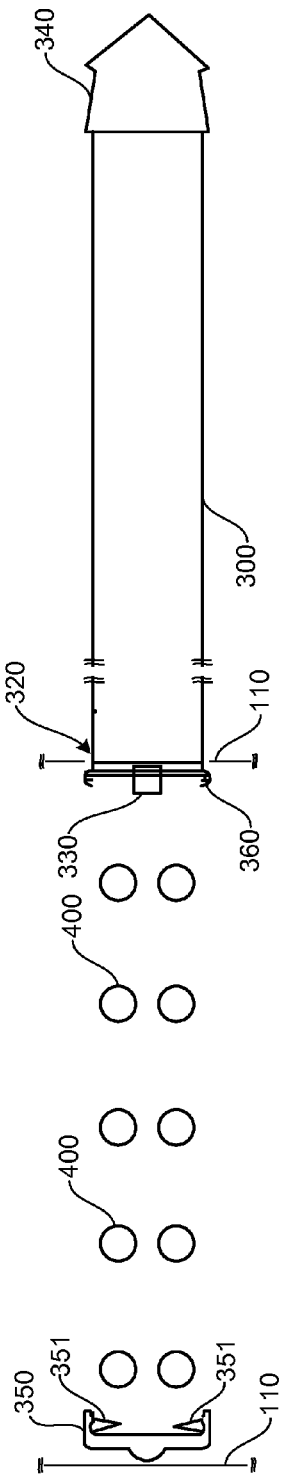

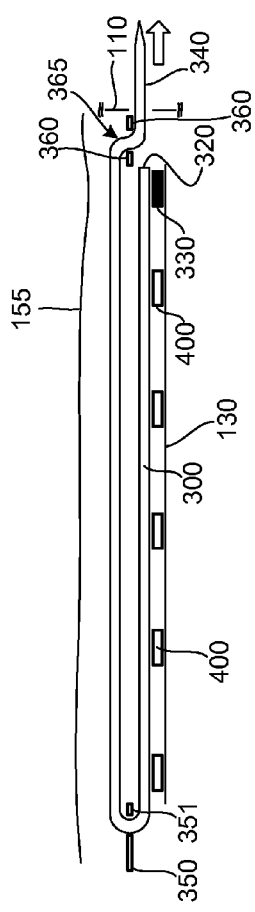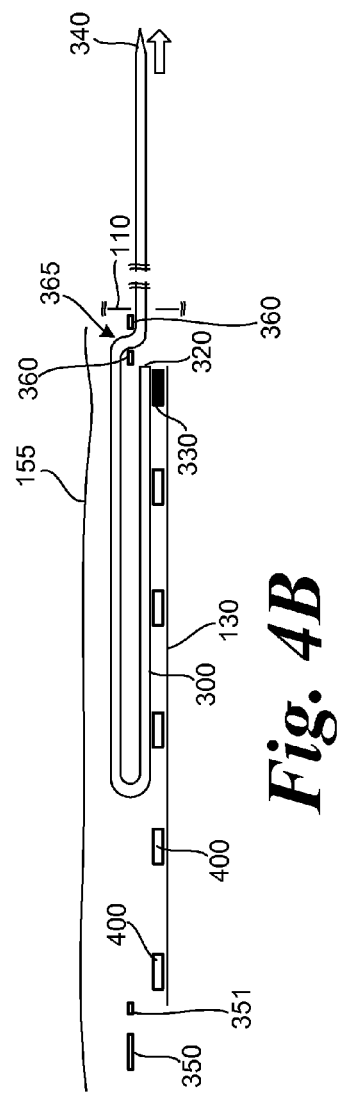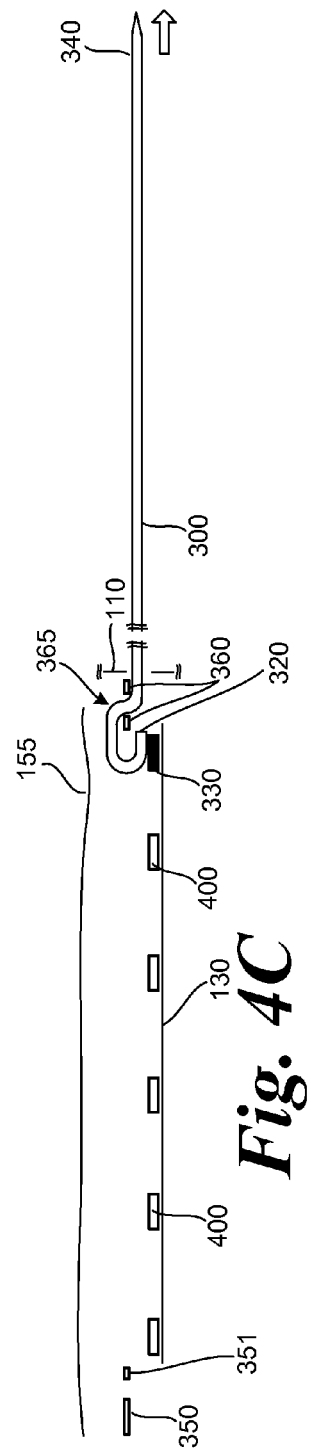

RELEASABLE LINER FOR SENSOR DEVICE

FIELD OF THE INVENTION

This invention relates generally to a protective liner for a sensor device and, more specifically, to a protective liner that may be controllably and systematically removed from a sensor device.

BACKGROUND OF THE INVENTION

Electrocardiogram (ECG) devices, using twelve (12) or more leads are known. Twelve-lead systems typically utilize individual leads that are connected to a patient, whereas ECG systems employing more than 12-leads are likely to be deployed in the form of an electrode vest, which is applied to the patient's torso. By way of example, one type of electrode vest is described in U.S. Pat. No. 6,055,448.

Electrodes for sensing bioelectric data or signals from a patient, whether connected to individual leads or in a multi-electrode vest require a conductive coupling gel placed between each electrode and the patient's skin. The gel better enables signal transfer between the patient's body and the electrode. The electrodes may also have an adhesive section to allow the electrodes to stay connected to the patient's skin during an ECG test. In addition, or alternatively, the conductive gel may have adhesive properties to allow the electrodes to adhere to the patient. Both the gel and adhesive section of an electrode must be protected from the environment until such time that the electrode is to be placed onto the patient. Individual protective patches that cover individual electrodes are known. The protective patches are removed by a medical clinician immediately prior to applying the electrodes to a patient. Alternatively, a single protective sheet may cover all of the electrodes on a vest. The protective sheet is removed immediately prior to placing the vest on a patient. Electrode vests may be unwieldy and difficult to apply to the patient and removing the individual protective patches or the larger protective sheet further complicates the utilization of such vests, making it difficult to place the vest and accompanying electrodes on the patient without the electrodes sticking to other parts of the vest or at the wrong locations on the patient.

SUMMARY OF THE INVENTION

According to an embodiment of the invention, a releasable liner for a sensor device having a plurality of electrodes includes a first strip portion configured to overlay and adhere to at least one of the plurality of electrodes, the first strip portion having a fixed end attached to the sensor device, and a second strip portion extending approximately parallel to the first strip portion and positioned adjacent thereto, the second strip portion having a free end movable relative to the fixed end of the first strip portion, the second strip portion coupled to the first strip portion such that a pulling force applied to the free end causes the first strip portion to separate from at least one of the plurality of electrodes.

According to another embodiment of the invention, a releasable liner for a sensor device includes a flexible sheet having a free end and a fixed end, and a portion of the flexible sheet that is releasably attached to the sensor device, wherein the flexible sheet is folded upon itself so that the fixed end is generally adjacent the free end. The liner is released from the sensor device when pulling force is exerted on the free end.

In accordance with yet another example of the invention, a sensor device for positioning on a human patient, includes a patient-facing surface with at least a portion of the patient-facing surface having an adhesive characteristic that may be removably attached to the patient's body and a protective liner folded upon itself and releasably affixed to the patient-facing surface of the sensor device. Exerting a pulling force on the liner causes the liner to release from the patient-facing surface of the sensor device.

In accordance with still another embodiment of the invention, a method for placing a sensor device in contact with a patient's anatomy includes the steps of positioning the sensor device on the patient in a desired position and releasing a protective sheet between the patent and a portion of the sensor device such that the releasing step exposes the sensor device to the patient's anatomy.

These and other examples of the invention will be described in further detail below.

BRIEF DESCRIPTION OF THE DRAWINGS

Preferred and alternative examples of the present invention are described in detail below with reference to the following drawings:

FIG. 3A is a schematic view of a portion of the liner covering electrodes on a sensor device;

FIG. 3B is a schematic view of a portion of the liner partially removed to partially expose electrodes on the sensor device;

FIG. 3C is a schematic view of a portion of the liner more fully removed to expose electrodes but still attached to the sensor device;

FIG. 4A is a schematic side view of the sensor device and liner of FIG. 3A;

FIG. 4B is a schematic side view of the sensor device and liner of FIG. 3B;

FIG. 4C is a schematic side view of the sensor device and liner of FIG. 3C; and, FIG. 5 is an exploded perspective view showing various components of the liner.

DETAILED DESCRIPTION OF THE PREFERRED EMBODIMENT

As previously discussed, conventional, single sheet protective liners for electrode vests used with electrocardiogram (ECG) devices are cumbersome and unwieldy to use, making the vest difficult to apply to a patient. Accordingly, there is a need for a releasable liner for such an electrode vest that may be easily and quickly removed from the electrodes in a controlled manner and which does not complicate the attachment of the vest or otherwise disturb the placement of the electrodes on the patient.

Figure 1:
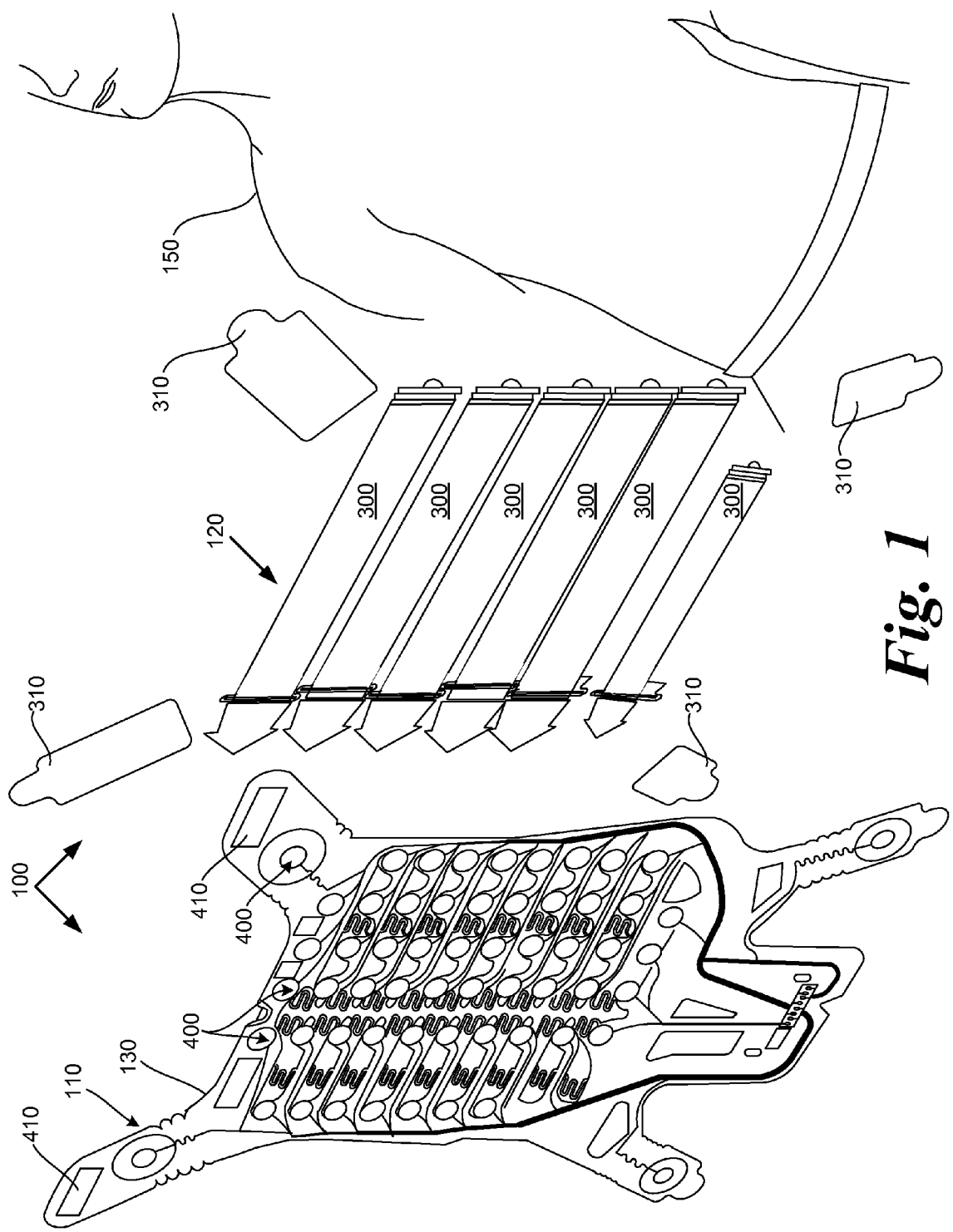
FIG. 1 is an exploded perspective view showing a sensor device and protective liner according to an embodiment of the present invention in relation to the front of a patient's body.

FIG. 1 illustrates an ECG sensor device 100 according to an embodiment of the present invention. Sensor device 100 includes an electrode vest 110 and protective liner 120. Vest 110 includes a plurality of sensors, or electrodes, 400 and conductive traces on a flexible dielectric membrane 130. The electrodes 400 are positioned on a patient-facing surface of the vest 110. For purposes of clarity, FIG. 1 is an exploded perspective view of the sensor device 100 that shows the liner 120 separated from the vest 110. However, it is to be understood that before the sensor device 100 is affixed to the patient 150, the liner 120 is in contact with the patient-facing side of vest 110 and covers the electrodes 400. In this way, the liner 120 protects the electrodes 400 until they are affixed to the patient 150.

Figure 2A:
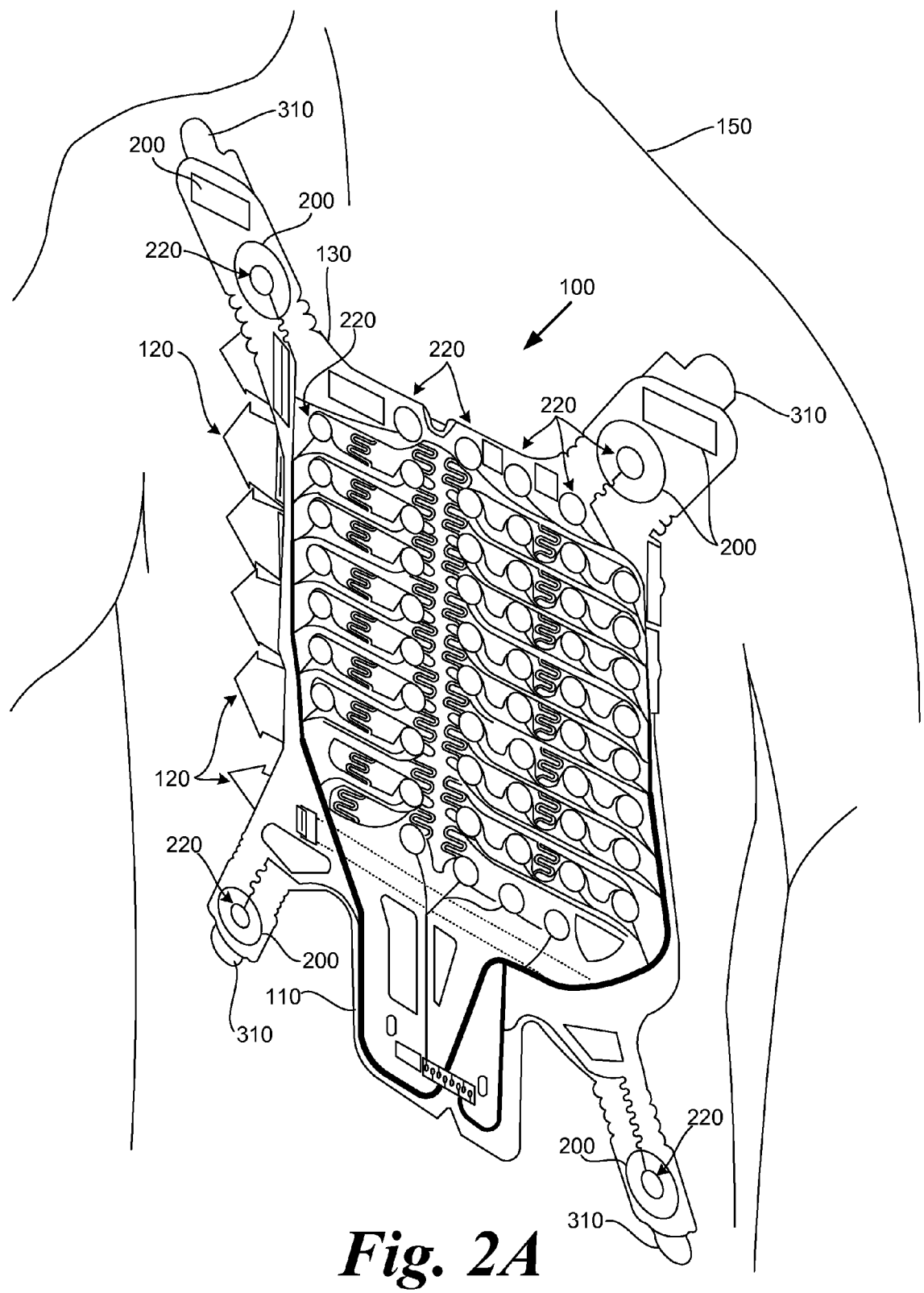
FIG. 2A is a perspective view of the sensor device and protective liner of FIG. 1 placed onto a patient.
Figure 2B:
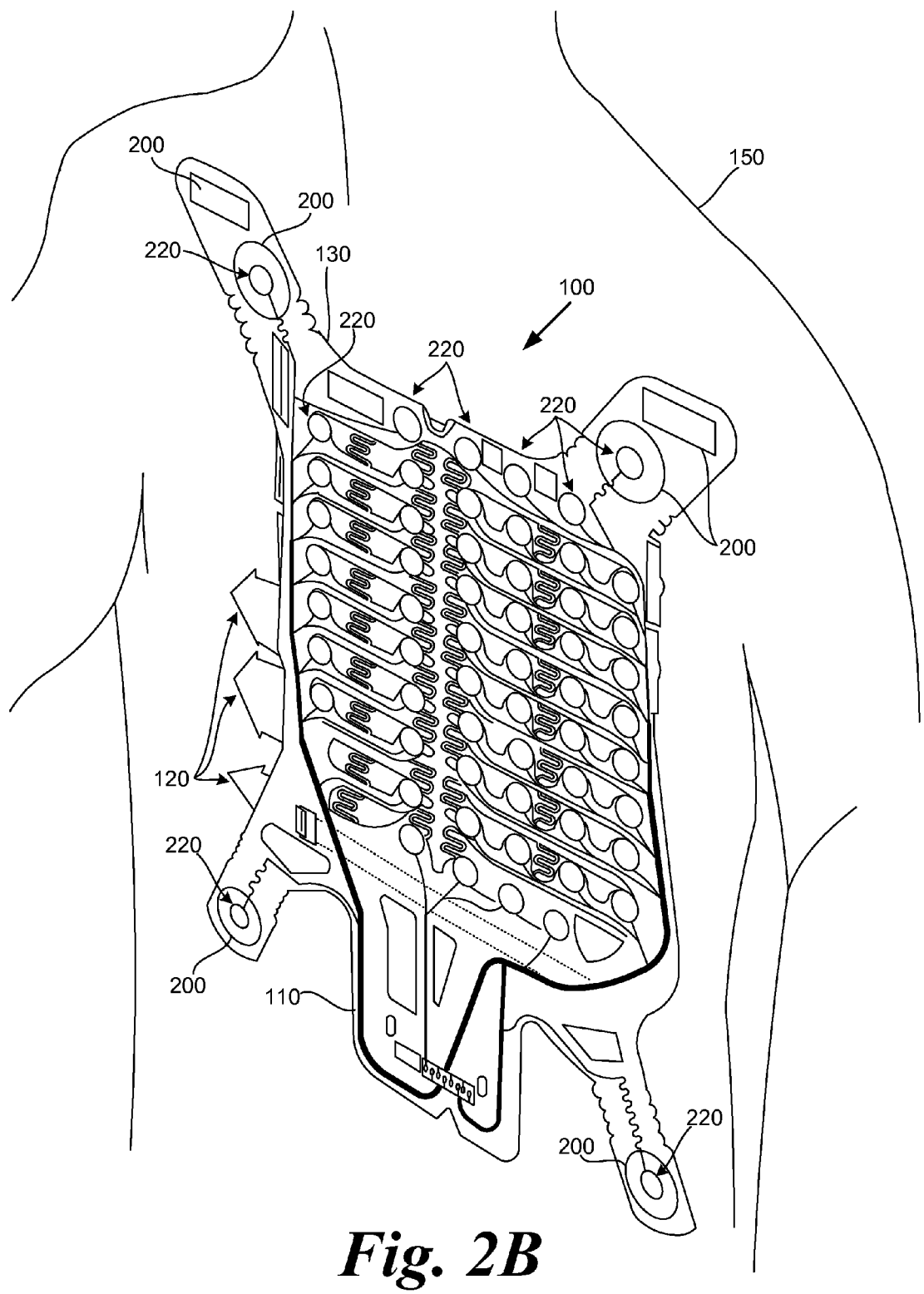
FIG. 2B is a perspective view of the sensor device and liner of FIG. 2A showing portions of the liner at various states of removal.
Figure 2C:
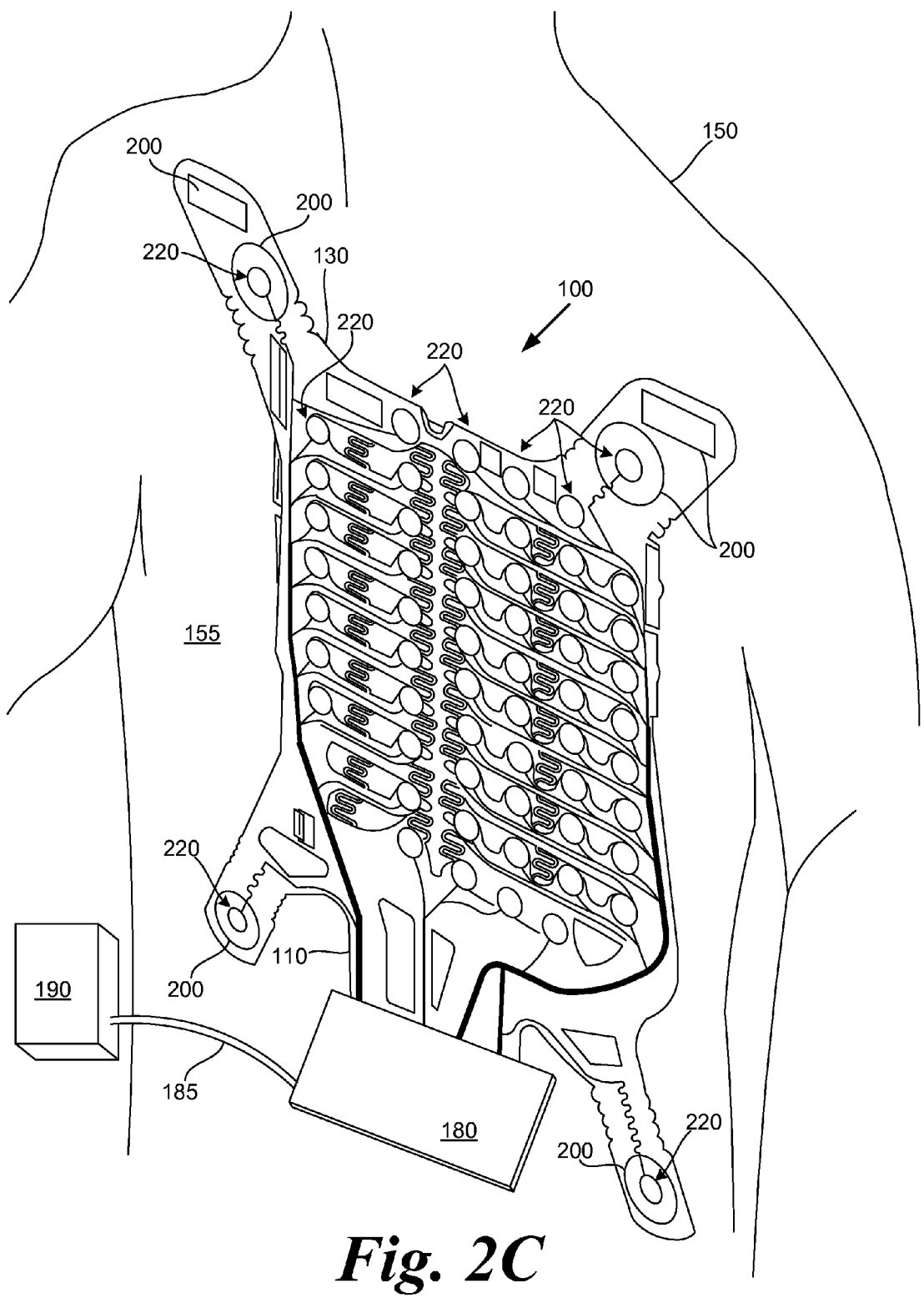
FIG. 2C is a perspective view of the sensor device and liner of FIG. 2A showing the liner entirely removed.

FIGS. 2A-C illustrate how the sensor device 100 may be attached to the patient 150 who is about to undergo a medical test, such as an ECG exam. In FIG. 2A, sensor device 100 is positioned over the front torso of the patient 150. The liner 120 is in contact with the patient-facing surface of the vest 110 and, as illustrated in FIG. 2A, the liner 120 is between the patient's skin and the electrode vest 110. Accordingly, the electrodes 400 in FIG. 2A are not in contact with the patient.

Turning to FIG. 2B, the sensor device 100 is shown partially attached to the patient 150. Portions of the liner 120 near the top of the vest 110, closest to the patient's head, have been removed from the vest 110 and the electrodes 400 in this area of the vest 110 are in contact with the patient's skin. FIG. 2C shows the remaining portions of liner 120 removed from the sensor device 100 and all of the electrodes 400 on the vest 110 are in contact with the patient 150. As depicted in FIG. 2C, the sensor device is now ready to be connected to a remote device, such as an ECG base unit 190. The electrodes 400 are electrically coupled to the ECG base unit 190 through connector 180 and cable 185.

As will be more fully appreciated from the following discussion and with reference to (FIG. 2C), the vest 110 and electrodes 400 in one embodiment of the present invention are held in place on the patient by adhesive patches 200 and adhesive gel 220 on or in the general vicinity of the electrodes 400. Conventional, conductive gel, such as Katecho KM10T or Covidien RG-63B, is suitable for coupling the electrodes to the patient and allowing electrical conductivity there between. Once the ECG or other medical test utilizing the sensor device 100 is completed, the vest 110 may be removed from the patient 150 by pulling the vest 110 away from the patient and, thus, peeling the electrodes 400 from the patient 150. The vest 110 may then be discarded.

As previously discussed, liner 120 is left attached to the vest 110 until the electrodes 400 are to be attached to the patient 150, thus preserving the cleanliness and integrity of the adhesive patches 200 and electrode gel 220.

As illustrated in FIGS. 2A-C, and more fully described below, liner 120 provides a quick and simple way to attach the electrode vest 110 in the proper position on the patient 150. Once the sensor device 100 is properly oriented on the patient (FIG. 2A), portions of the protective liner 120 are removed to allow the medical personnel to attach the vest 110 and electrodes 400 to the patient 150 in a controlled manner.

FIG. 2B shows the vest 110 partially affixed to the patient 150. Preferably, the clinician removes some or all of patches 310 and affixes the associated adhesive patches and gel 200, 220 to the patient 150 to hold the vest 110 in the proper orientation. Starting near the top of the sensor device 100, closest to the patient's head, portions of the liner 120, illustrated as a series of strips, are removed and the corresponding portions of the vest 110 and electrodes 400 are pressed into place onto the patient's skin by the medical clinician. Continuing to work down the vest 110, away from the patient's head, the medical personnel removes the strips of the liner 120 and affix the vest 110 and the uncovered electrodes 400 to the patient 150. Once the liner 120 is completely removed, that is, once all of the strips have been removed (FIG. 2C), the vest 110 may then be connected to the remote equipment, such as the ECG base unit 190 to begin the desired medical test. After the test is completed, the medical personnel may remove the vest 110 from the patient 150 and discard it in an appropriate and conventional manner.

In one embodiment, as briefly discussed above, liner 120 includes a number of releasable, protective strips 300 (FIG. 1). The liner 120 may also include additional, releasable patches 310 positioned on extensions of the vest 110 that may cover electrodes 400 and/or adhesive patches 410 for securing the vest 110 to the patient 150. When medical personnel apply the vest 110 to the patient 150, the patches 310 near the patient's head may be removed first to allow the medical technician to place the vest 110 on the patient 150 and hold it in proper orientation. Similarly, the patches 310 near the bottom of the vest 110, farthest away from the patient's head, may be removed next to further secure the vest 110 and electrodes 400 to the patient 150. The patches 310 may be removed in this or a different order relative to each other and the liner strips 300 as preferred by the medical technician.

FIGS. 3A-C show one of the protective liner strips 300 during various stages of release from the vest 110. FIGS. 4A-C are schematic side views of the liner strip 300 in the various stages of removal illustrated in corresponding FIGS. 3A-C, and further illustrate the release of the liner strip 300 from the vest 110. FIGS. 3A-C illustrate the liner strip 300 as viewed from the patient's side of the vest 110 while FIGS. 4A-4C illustrate corresponding side elevational views of the liner strip 300.

In FIG. 3A, the liner strip 300 is placed on the vest 110 covering rows of electrodes 400. The liner strip 300 includes a fixed end 320 releasably attached to the vest 110 by a fastening device 330, which may take the form of, but is not limited to, adhesive tape, wax, hook and loop fasteners, magnets, etc. The liner strip 300 further includes a free end 340 that passes through a retainer 350 located distally from the fixed end 320 and then passes through a guide 360 located proximate the free end 340, thus forming an open loop as best shown in FIG. 4A. As illustrated in FIGS. 3A-C and as discussed with reference to FIG. 5, retainer 350 and guide 360 are attached to vest 110.

Referring specifically to FIG. 4A, liner strip 300 is positioned between electrodes 400 and the patient's skin 155. The liner strip 300 is attached at its fixed end 320 to dielectric membrane 130 by the fastening device 330 and passes through the retainer 350. As previously discussed, the liner strip 300 is folded back on itself after passing through retainer 350 and may pass through a slot 365 in guide 360 so that free end 340 is looped back to the general proximity of, and even extending past, the fixed end 320.

Turning to FIGS. 3B and 4B, free end 340 has been pulled away from the fixed end 320. As oriented in FIGS. 3B and 4B, free end 340 has moved to the left. This motion is accomplished by the medical technician pulling on free in 340. As the free end 340 is pulled, the liner strip 300 disengages from the retainer 350. The material properties and mechanical design of the retainer 350 allow it to give way and release the strip 300 when a sufficient pulling force is applied to end 340. As end 340 is pulled, the strip 300 pulls away from retainer 350 and sequentially and controllably releases from, and exposes, electrodes 400. As the strip 300 continues to be pulled, eventually, all electrodes 400 previously covered by strip 300 are uncovered and exposed to the patient 150 (FIGS. 3C and 4C). Continued pulling by medical personnel causes the liner strip 300 to eventually release completely from vest 110. As discussed above, and with reference to FIG. 2B, a medical technician may apply pressure to the vest 110 in the area of the exposed electrodes 400 so that they better adhere to the patient 150.

As the free end 340 of liner strip 300 is pulled, arms 351 of retainer 350 flex and release the liner strip 300 (FIG. 3B). As the medical personnel continues to pull the liner strip 300, the strip releases from, and uncovers electrodes 400. The uncovered electrodes 400 may be pressed into contact with the patient's skin 155. In FIG. 3C, the liner strip 300 has been pulled sufficiently far to uncover all previously covered electrodes 400, but is still attached to the vest 110 at its fixed end 320 by tape 330. Continued pulling of strip 300 releases the end 320 from the vest 110. The tape may either remain on the vest 110 or on the liner strip 300. All electrodes 400 previously covered by strip 300 are now uncovered and are in contact with the patient 150.

Figure 5:
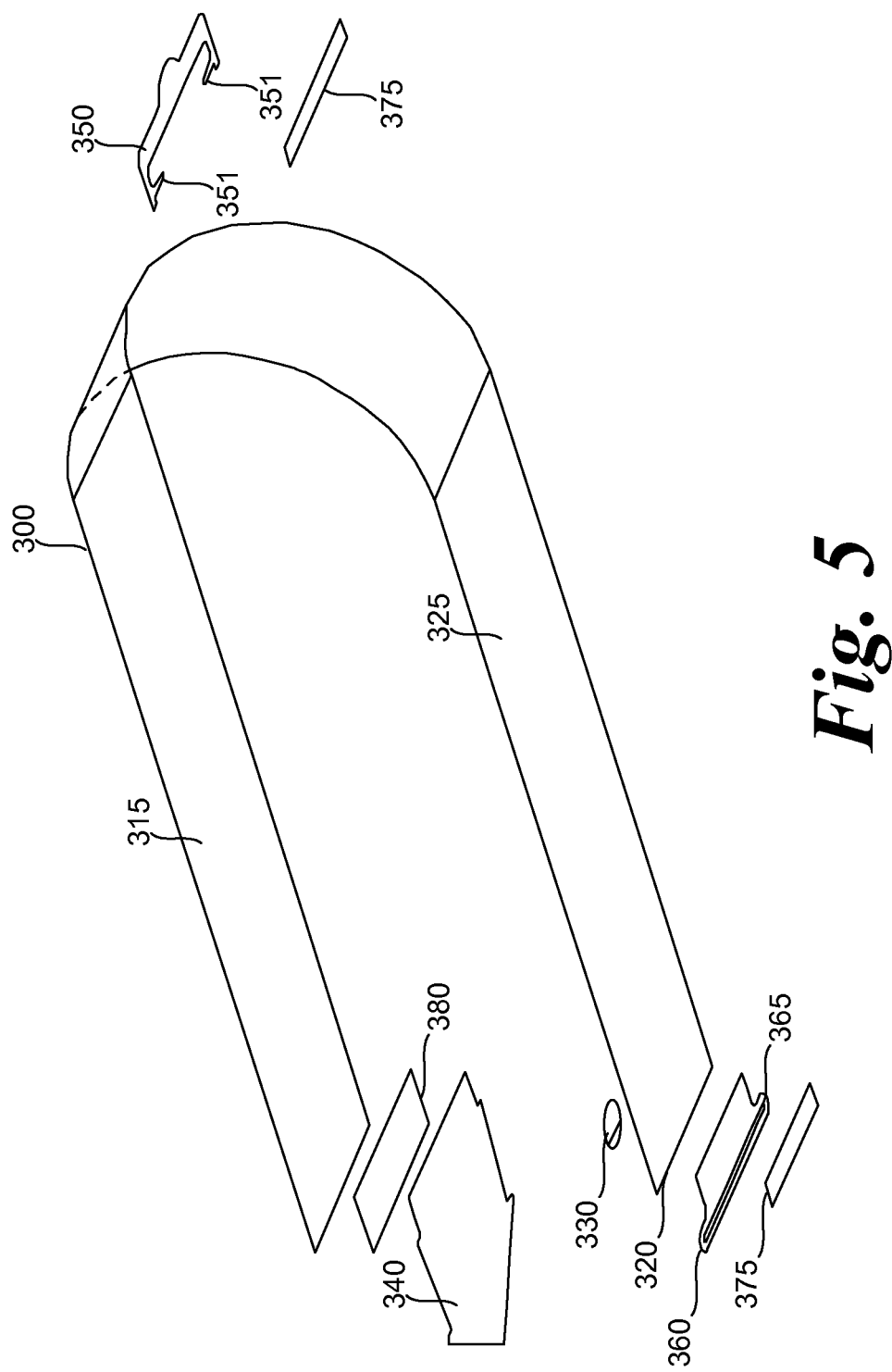

FIG. 5 illustrates one embodiment of a liner strip 300. In this embodiment, retainer 350 and guide 360 are elements affixed to vest 110 (FIGS. 1 and 2A) by adhesive strips 375. Alternatively, the retainer 350 and guide 360 may be attached to the vest 110 by other means, including but not limited to gluing or sonic welding. In the embodiment illustrated in FIG. 5, free end 340 has an arrowhead shape and is attached to the liner strip 300 by adhesive 380. Free end 340 may have other shapes and may be attached to the liner strip 300 by other means, such as gluing or sonic welding. Further, end 340 may be formed as an integral part of liner strip 300. One benefit of the arrowhead shape of end 340 is that the width of end 340 is larger than the width of slot 365 in guide 360 through which the liner strip 300 passes. This geometry prevents the free end 340 of liner strip 300 from unintentionally pulling back through the guide 360. It is further understood that retainer 350 and guide 360 may be formed as part of, and integral with, vest 110. For example, the retainer 350 and guide 360 may be laser cut into the dielectric substrate 130 of vest 110.

Preferably, a surface 315 (FIG. 5) of liner strip 300 has sufficiently low adhesive properties that allow it to release from the adhesive gel on the electrodes 400 when an appropriate pulling force is applied to free end 340. For example, silicone coated polyester release liner materials may offer these properties. Also preferably, the opposite surface 325 of liner strip 300 has sufficiently low coefficient of friction properties to allow it to slide easily against itself when a pulling force is applied to free end 340 (also FIG. 5).

While the preferred embodiment of the invention has been illustrated and described, as noted above, many changes can be made without departing from the spirit and scope of the invention. For example, the protective liner may be shaped other than as a series of strips and there may be more than one guide element along the liner strip. The characteristics of the protective liner material may be such that there is no need for a retainer or guide. For example, the liner may be stiff enough to hold its place on the vest without the need for a retainer. By way of further example, the length of the liner strip may be short enough that a guide is not required. Accordingly, the scope of the invention is not limited by the disclosure of the preferred embodiment. Instead, the invention should be determined entirely by reference to the claims that follow.

The embodiments of the invention in which an exclusive property or privilege is claimed are defined as follows:

1. A sensor device comprising:
    an electrode vest having a plurality of electrodes;
    a guide fixed to the electrode vest;
    a retainer fixed to the electrode vest;
    a protective liner comprising a continuous strip folded onto itself to form a first strip portion and a second strip portion, the first strip portion releasably attached to at least one of the plurality of electrodes, the first strip portion having a fixed end portion attached to the electrode vest and a second end portion engaged with the retainer, and the second strip portion includes a first end portion coupled to the second end portion of the first strip portion proximate the retainer and a second, free end portion that extends through the guide, the second strip portion having a second strip surface in contact with a skin surface of a patient when the sensor device is placed onto the patient,
    wherein a pulling force applied to the second, free end portion causes the first strip portion to separate from at least one of the plurality of electrodes,
    wherein the pulling force causes the continuous strip to disengage from the retainer, and
    wherein the second strip surface includes a low coefficient of friction to minimize abrasion of the skin surface when the pulling force is applied.

2. The sensor device of claim 1, further comprising a second surface of the first strip portion and the second strip portion positioned between the free and fixed ends having a first section and a second section that face away from each other when the protective liner is folded upon itself.

3. A method for placing a sensor device in contact with a patient's anatomy, the method comprising the steps of:
    positioning the sensor device on the patient in a desired position, the sensor device having a plurality of electrodes, a guide, a retainer, and a continuous protective liner folded onto itself to form at least two strips wherein one strip is coupled to the plurality of electrodes and attached to the sensor device while the other strip is in contact with a skin surface of a patient; and
    applying a pulling force to a free end of the other strip to release the continuous protective liner from the retainer and separate the one strip from the plurality of electrodes, wherein applying the pulling force includes
    generating relative motion between the continuous protective liner and the patient's anatomy, and wherein the other strip includes a low-friction, contact surface for preventing abrasion between the other strip and the patient's anatomy during the relative motion.

4. The method of claim 3, wherein applying the pulling force includes pulling on the free end of the other strip in a direction in which the pulling force is generally coplanar with a surface of the sensor device.

5. The method of claim 3, wherein applying the pulling force causes arms of the retainer to flex and release the continuous protective liner.

* * * * *